United States Patent [19]
Bös et al.

[11] Patent Number: 5,955,495
[45] Date of Patent: *Sep. 21, 1999

[54] METHOD OF TREATING DISEASES OF THE CNS

[75] Inventors: Michael Bös; Heinz Stadler, both of Rheinfelden, Switzerland; Jürgen Wichmann, Steinen, Germany

[73] Assignee: Hoffmann-La Roche Inc., Nutley, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/837,140

[22] Filed: Apr. 14, 1997

[51] Int. Cl.$^6$ ..................................................... A61K 31/34
[52] U.S. Cl. .......................... 514/469; 514/468; 549/467
[58] Field of Search ............................ 549/467; 514/469, 514/468

[56] References Cited

FOREIGN PATENT DOCUMENTS 0 352 832  1/1990  European Pat. Off. .

OTHER PUBLICATIONS

Takagi et al, J. Jpn. Broncho–Esophagol Soc. 42 (3), pp. 244–250, Biosis Abs. 91:415162 (1991).
Khimiko–Farmatsevticheski Zhurnal vol. 18, No. 11 pp. 1309–1313 (1984).
Eur. J. Med. Chem. Chim. Ther. 1982 No. 6, pp. 577–581.
Indian J. Chem. Sect. B (1979) 18B(3), pp. 254–256.
Synthesis & Psychotrophic Activity of 2–Phenoxy–propionamidoximes and their Analogs—Voronina et al., pp. 750–754, Eng. Translation From Khimiko–Farm. Zhurnal, vol. 18(11), pp. 1309–1313 (1984).
Chem. Abstracts, vol. 92, No. 9, 76203 Mar. 3, 1980.

*Primary Examiner*—Bernard Dentz
*Attorney, Agent, or Firm*—George W. Johnston; Patricia S. Rocha-Tramaloni; Robert A. Silverman

[57] ABSTRACT

The invention is concerned with the use of compounds of the general formula

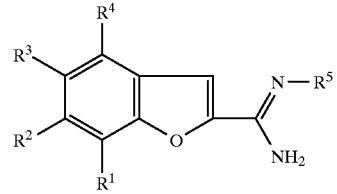

wherein $R^1$–$R^4$ signify hydrogen, halogen, lower-alkyl, lower-alkoxy, aryl, benzyloxy, lower-alkoxy-lower-alkyl, lower-alkyl-sulphanyl, lower-alkyl-sulphanyl-lower-alkyl or $R^1$ and $R^2$ together signify the group —O—(CH$_2$)$_2$— or —(CH$_2$)$_2$—O— and $R^5$ signifies hydrogen or hydroxy, as well as their pharmaceutically acceptable salts in the control or prevention of illnesses or disorders of the central nervous system such as migraine, schizophrenia, anxiety states, sleep disorders, anorexia, Alzheimer's disease, addictions (alcohol, nicotine, benzodiazepine, cocaine, etc.), as well as disorders which result from damage to the head/brain or to the spinal column/bone marrow and, respectively, for the production of corresponding medicaments.

18 Claims, No Drawings

METHOD OF TREATING DISEASES OF THE CNS

SUMMARY OF THE INVENTION

The invention is concerned with compounds of the formula

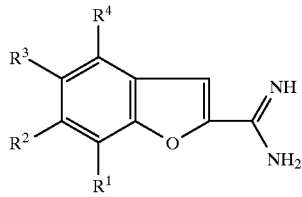

IA wherein
- $R^1$ and $R^4$ signify hydrogen and $R^2$ and $R^3$ signify fluorine, or
- $R^1$–$R^3$ signify hydrogen and $R^4$ signifies ethoxy, or
- $R^1$ signifies methoxy and $R^2$–$R^4$ signify hydrogen, or
- $R^1$ signifies ethoxy and $R^2$–$R^4$ signify hydrogen, or
- $R^1$, $R^2$ and $R^4$ signify hydrogen and $R^3$ signifies fluorine, or
- $R^1$, $R^3$ and $R^4$ signify hydrogen and $R^2$ signifies fluorine, or
- $R^1$ signifies methyloxyethyl and $R^2$–$R^4$ signify hydrogen, or
- $R^1$ signifies n-propyl, $R^2$ signifies fluorine and $R^3$ and $R^4$ signify hydrogen, or
- $R^1$ and $R^3$ signify hydrogen and $R^2$ and $R^4$ signify fluorine, or
- $R^1$ signifies n-propyl, $R^4$ signifies fluorine and $R^2$ and $R^3$ signify hydrogen or
- $R^1$ signifies bromine, $R^4$ signifies fluorine and $R^2$ and $R^3$ signify hydrogen, or
- $R^1$–$R^3$ signify hydrogen and $R^4$ signifies fluorine, or a pharmaceutically acceptable salt thereof.

The invention also concerns pharmaceutical compositions comprising a compound of formula IA or a pharmaceutically acceptable salt thereof, and an inert carrier material.

The invention is also concerned with compounds of the formula

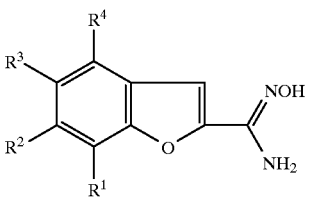

IB wherein
- $R^1$ and $R^4$ signify hydrogen and $R^2$ and $R^3$ signify fluorine, or $R^1$ signifies ethoxy and $R^2$–$R^4$ signify hydrogen, or $R^1$, $R^2$ and $R^4$ signify hydrogen and $R^3$ signifies fluorine, or $R^1$, $R^3$ and $R^4$ signify hydrogen and $R^2$ signifies fluorine or $R^1$ signifies methyloxyethyl and $R^2$–$R^4$ signify hydrogen, or a pharmaceutically acceptable salt.

The invention also concerns pharmaceutical compositions comprising a compound of formula IB or a pharmaceutically acceptable salt thereof, and an inert carrier material.

The invention is also concerned with a method of controlling or preventing illness or disorders of the central nervous system. The method comprises administering to a host in need of such control or prevention an effective amount of a compound of the formula

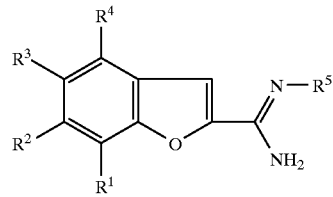

I wherein
- $R^1$–$R^4$ are, independently, hydrogen, halogen, lower-alkyl, lower-alkoxy, aryl, benzyloxy, lower-alkoxy-lower-alkyl, lower-alkyl-sulphanyl, lower-alkyl-sulphanyl-lower-alkyl or $R^1$ and $R^2$ together are the group —O—(CH$_2$)$_2$— or (CH$_2$)$_2$—O—; and
- $R^5$ is hydrogen or hydroxy, or a pharmaceutically acceptable salt.

It has been found that the compounds of formula I, including the compounds of formula IA and IB, are useful for the prevention and treatment of illnesses and disorders such as migraine, schizophrenia, anxiety states, sleep disorders, anorexia, Alzheimer's disease, addictions (alcohol, nicotine, benzodiazepine, cocaine, and the like), as well as disorders which result from damage to the head/brain or to the spinal column/bone marrow.

DETAILED DESCRIPTION OF THE INVENTION

The invention is concerned with benzofuryl derivatives of the formula

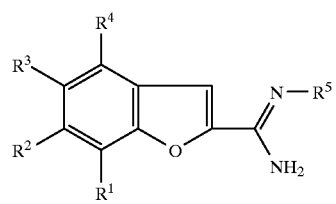

I wherein
- $R^1$–$R^4$ signify hydrogen, halogen, lower-alkyl, lower-alkoxy, aryl, benzyloxy, lower-alkoxy-lower-alkyl, lower-alkyl-sulphanyl, lower-alkyl-sulphanyl-lower-alkyl or $R^1$ and $R^2$ together signify the group —O—(CH$_2$)$_2$— or —(CH$_2$)$_2$—O— and
- $R^5$ signifies hydrogen or hydroxy, as well as their pharmaceutically acceptable salts.

Some of these compounds are described in EP 0 352 832 for use as broncopulmonary active substances, especially for the treatment of asthma. Furthermore, the unsubstituted amidoxime is known as an antidepressant (Khim. Farm. Zhurnal, vol. 18, No. 11, pp. 1309–1313, 1984). Moreover, analgesic, inflammation-inhibiting and ulcerogenic properties of certain 2-benzofurylamidoxime derivatives are described in Eur. J. Med. Chem., No. 6, 1982, pp. 577–581.

It has surprisingly been found that the compounds of formula I have a strong affinity to serotonin receptors, primarily to the 5-$HT_{2C}$ and 5-$HT_{2A}$ receptors, and are accordingly suitable for the treatment of illnesses or disorders of the central nervous system.

Objects of the present invention are the use of compounds of formula I and of pharmaceutically usable salts thereof for the control or prevention of illnesses or disorders of the central nervous system such as migraine, schizophrenia, anxiety states, sleep disorders, anorexia, Alzheimer's disease, addictions (alcohol, nicotine, benzodiazepine, cocaine, etc.), as well as disorders which result from damage to the head/brain or to the spinal column/bone marrow and, respectively, for the production of corresponding medicaments.

Further objects of the present invention are compounds of formula IA and compounds of formula IB, and their salts, their use as therapeutically active substances, the manufacture of the novel compounds and salts as well as medicaments based thereon and the production of such medicaments.

The term "lower-alkyl" used in the present description denotes straight-chain or branched-chain saturated hydrocarbon residues such as methyl, ethyl, n-propyl, isopropyl, n-butyl, isobutyl, s-butyl, t-butyl and the like with up to 7 carbon atoms. The terms "lower-alkoxy" denotes an alkyl residue in the sense of the foregoing definition bonded via an oxygen atom.

"Halogen" can signify fluorine, chlorine, bromine or iodine.

"Aryl" in the present description signifies phenyl and the like.

The term "pharmaceutically acceptable salts" embraces salts with inorganic and organic acids such as hydrochloric acid, hydrobromic acid, sulphuric acid, phosphoric acid, citric acid, formic acid, maleic acid, acetic acid, succinic acid, tartaric acid, methanesulphonic acid, p-toluenesulphonic acid and the like.

The binding of the compounds of formula I in accordance with the invention to selected serotonin receptors was determined in vitro by standard methods. It was thereby found that the amidines of the formula

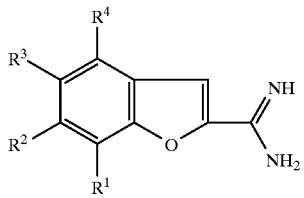

wherein $R^1$–$R^4$ are, independently, hydrogen, halogen, lower-alkyl, lower-alkoxy, aryl, benzyloxy, lower-alkoxy-lower-alkyl, lower-alkyl-sulphonyl, lower-alkyl-sulphenyl-lower-alkyl or $R^1$ and $R^2$ together are the group —O—$(CH_2)_2$ or $(CH_2)_2$—O— show good activities in vitro, while the amidoximes of the formula

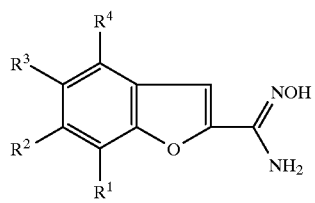

wherein $R^1$–$R^4$ are, independently, hydrogen, halogen, lower-alkyl, lower-alkoxy, aryl, benzyloxy, lower-alkoxy-lower-alkyl, lower-alkyl-sulphonyl, lower-alkyl-sulphenyl-lower-alkyl or $R^1$ and $R^2$ together are the group —O—$(CH_2)_2$ or $(CH_2)_2$—O— are only active in vivo. As prodrugs the amidoximes have no affinity to the 5-$HT_{2C}$ receptor. However, they are converted in vivo into the corresponding amidines.

Especially preferred compounds from the group of amidines of formula I are the following:
5,6-difluorobenzofuran-2-carboxamidine;
4-ethoxybenzofuran-2-carboxamidine;
7-methoxybenzofuran-2-carboxamidine;
7-ethoxybenzofuran-2-carboxamidine;
5-fluorobenzofuran-2-carboxamidine;
6-fluorobenzofuran-2-carboxamidine;
7-ethoxymethylbenzofuran-2-carboxamidine;
6-fluoro-7-propylbenzofuran-2-carboxamidine;
4-fluorobenzofuran-2-carboxamidine and
benzofuran-2-carboxamidine.

Especially preferred compounds form the group of amidoximes of formula I the following:
5,6-difluorobenzofuran-2-carboxamidoxime;
7-ethoxybenzofuran-2-carboxamidoxime;
5-fluorobenzofuran-2-carboxamidoxime;
6-fluorobenzofuran-2-carboxamidoxime;
7-ethoxymethylbenzofuran-2-carboxamidoxime and
benzofuran-2-carboxamidoxime.

The manufacture of the new compounds of formula IA can be effected by
a) reacting a compound of the formula

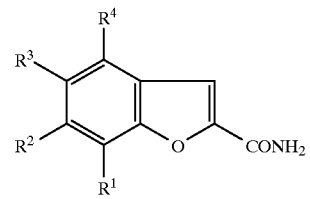

wherein
$R^1$ and $R^4$ signify hydrogen and $R^2$ and $R^3$ signify fluorine, or
$R^1$–$R^3$ signify hydrogen and $R^4$ signifies ethoxy, or
$R^1$ signifies methoxy and $R^2$–$R^4$ signify hydrogen, or
$R^1$ signifies ethoxy and $R^2$–$R^4$ signify hydrogen, or
$R^1$, $R^2$ and $R^4$ signify hydrogen and $R^3$ signifies fluorine, or
$R^1$, $R^3$ and $R^4$ signify hydrogen and $R^2$ signifies fluorine, or
$R^1$ signifies methyloxyethyl and $R^2$–$R^4$ signify hydrogen, or
$R^1$ signifies n-propyl, $R^2$ signifies fluorine and $R^3$ and $R^4$ signify hydrogen, or
$R^1$ and $R^3$ signify hydrogen and $R^2$ and $R^4$ signify fluorine, or
$R^1$ signifies n-propyl, $R^4$ signifies fluorine and $R^2$ and $R^3$ signify hydrogen or
$R^1$ signifies bromine, $R^4$ signifies fluorine and $R^2$ and $R^3$ signify hydrogen, or
$R^1$–$R^3$ signify hydrogen and $R^4$ signifies fluorine, with an oxonium salt, preferably with triethyloxonium tetrafluoroborate, and subsequently treating with an ammonium halide, or b) converting a compound of the formula

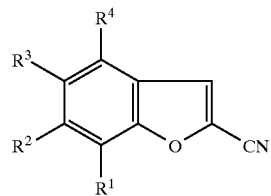

wherein $R^1$–$R^4$ have the significances set forth under a), with $H_2S$ gas into a corresponding thioamide and subsequently reacting this with an ammonium salt in the presence of an alkyl halide, or c) hydrogenating a compound of formula IB in which $R^1$–$R^4$ have the significances set forth under a), and d) if desired, converting a compound of formula IA into a pharmaceutically acceptable salt.

The manufacture of the especially preferred compounds of formula IB can be effected by e) reacting a compound of formula III in which $R^1$ and $R^4$ signify hydrogen and $R^2$ and $R^3$ signify fluorine, or $R^1$ signifies ethoxy and $R^2$–$R^4$ signify hydrogen, or $R^1$, $R^2$ and $R^4$ signify hydrogen and $R^3$ signifies fluorine, or $R^1$, $R^3$ and $R^4$ signify hydrogen and $R^2$ signifies fluorine or $R^1$ signifies methyloxyethyl and $R^2$–$R^4$ signify hydrogen with hydroxylamine, and f) if desired, converting a compound of formula IB into a pharmaceutically acceptable salt.

A more detailed description of process variants a), d) and e) set forth above is given in Examples 1–18. The starting materials are known or can be prepared in a known manner illustrated in the Examples hereinafter or in analogy thereto.

In accordance with process variant b) for the manufacture of amidine compounds of formula IA, compounds of formula III are firstly converted into a corresponding thioamide by conducting a $H_2S$ stream through a mixture consisting of a compound of formula III, pyridine and triethylamine. Then, the thioamide is treated with an alkyl halide, for example with methyl iodide, and subsequently reacted with an ammonium salt, preferably with ammonium acetate.

The hydrogenation according to variant c) is effected according to generally usual methods, preferably with Ra-Ni in an ethanol/acetic acid mixture.

The following Scheme illustrates the manufacture of compounds of formula I.

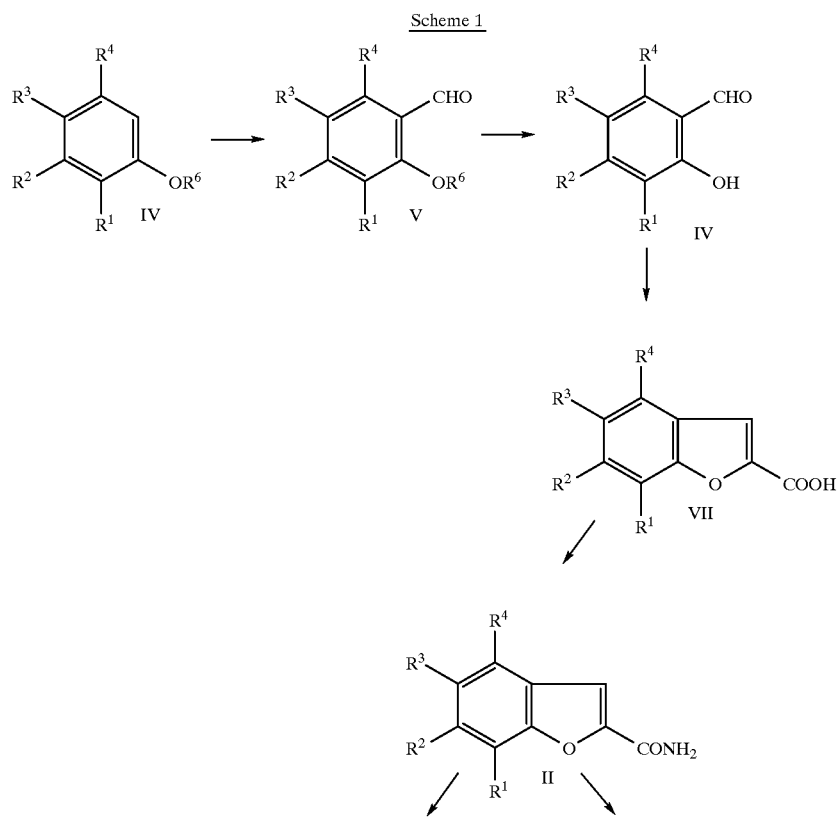

Scheme 1

-continued

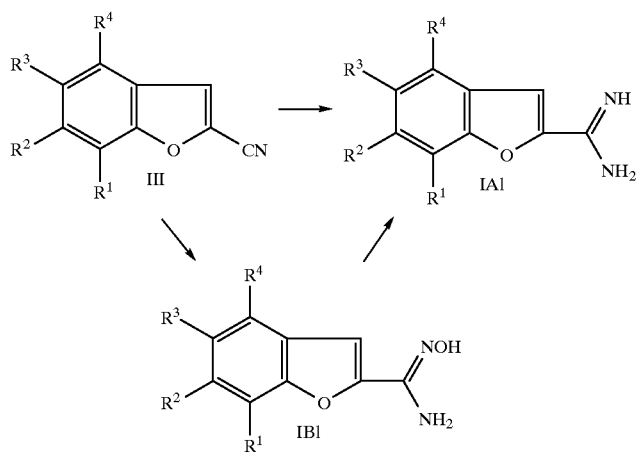

In Scheme I, $R^1$–$R^4$ are, independently, hydrogen, halogen, lower-alkyl, lower-alkoxy, aryl, benzyloxy, lower-alkoxy-lower-alkyl, lower-alkyl-sulphonyl, lower-alkyl-sulphenyl-lower-alkyl or $R^1$ and $R^2$ together are the group —O—$(CH_2)_2$ or $(CH_2)_2$—O— and $R^6$ signifies lower alkyl.

In Scheme I, the compounds of formula IV are known or can be prepared by known methods.

As mentioned earlier, the compounds of formula I have valuable pharmacological properties, since they have a strong binding to serotonin receptors, primarily to 4-$HT_{2C}$ and 5-$HT_{2A}$ receptors, and are accordingly suitable for the treatment or prevention of illnesses or disorders of the central nervous system such as migraine, schizophrenia, anxiety states, sleep disorders, anorexia, Alzheimer's disease, addictions (alcohol, nicotine, benzodiazepine, cocaine, etc.), as well as disorders which result from damage to the head/brain or to the spinal column/bone marrow.

The binding of compounds of formula I in accordance with the invention to selected serotonin inhibitors was determined in vitro by standard methods. The preparations were investigated in accordance with the tests given hereinafter:

a) Affinity to the 5-$HT_{2C}$ receptor in accordance with the [3H]-5-HT binding assay according to the method of S.J. Peroutka et al., Brain Research 584, 191–196 (1992).

b) Affinity to the 5-$HT_{2A}$ receptor in accordance with the [3H]- DOB binding assay according to the method of T. Branchek et. al., Molecular Pharmacology 38, 604–609 (1990).

The Pki values (Pki=-log10 $K_i$) of the test substances are given. The Ki value is defined by the following formula:

$$Ki = \frac{IC_{50}}{1 + \frac{[L]}{K_D}}$$

with the $IC_{50}$ values being those concentrations of test compounds in nM at which 50% of the receptor-bonded ligands are displaced. [L] is the ligand concentration and the $K_D$ value is the dissocation constant of the ligand.

The thus-determined activity of some compounds in accordance with the invention will be evident from the following

TABLE

| Example No. | $R^1$ | $R^2$ | $R^3$ | $R^4$ | $R^5$ | 5-$HT_{2C}$ Method a | 5-$HT_{2A}$ Method b |
|---|---|---|---|---|---|---|---|
|  | H | OMe | H | H | H | 6.2 | 5.2 |
|  | H | H | OMe | H | H | 5.6 | <5 |
|  | H | H H | H | OMe | H | 6.8 | 5.7 |
|  | Me | H | H | H | H | 6.4 | 5.6 |
|  | H | Me | H | H | H | 6.0 | <5 |
|  | Cl | H | H | H | H | 6.8 | 5.4 |
|  | H | Cl | H | H | H | 5.9 | 5.3 |
|  | H | H | Cl | H | H | 5.8 | 5.8 |
|  | F | H | H | H | H | 6.1 | 5.3 |
|  | H | H | H | H | H | 7.1 | 5.3 |
|  | CH | H | H | H | H | 6.2 | <5 |
|  | Oi-Pr | H | H | H | H | 6.7 | 6.0 |
|  | OPr | H | H | H | H | 6.8 | <5 |
|  | OBn | H | H | H | H | 7.2 | 6.9 |
|  | O-Cyclo-hex | H | H | H | H | 6.2 | 6.8 |
|  | Oi-Bu | H | H | H | H | 5.7 | 6.0 |
|  | Oi-Pent | H | H | H | H | 6.3 | 6.8 |
|  | O-Cyclo-pent | H | H | H | H | 6.3 | 6.6 |
|  | Ph | H | H | H | H | 6.6 | 6.8 |
|  | Cl | H | Cl | H | H | 5.6 | 6.2 |
|  | Br | H | Br | H | H | 5.7 | 6.5 |
|  | Br | H | Cl | H | H | 5.3 | 6.5 |
|  | i-Prop | H | H | H | H | 7.2 | 6.1 |
|  | OMe | H | Br | H | H | 6.9 | 5.6 |
|  | OMe | H | Ph | H | H | 5.8 | 6.8 |
|  | n-Pr | H | H | H | H | 7.1 | 6.0 |
|  | OMe | H | H | Me | H | 7.0 | 5.6 |
|  | $CH_2$—O-Me | H | H | H | H | 6.8 | 5.5 |
|  | $CH_2$—O-iPr | H | H | H | H | 6.4 | 5.7 |
|  | $CH_2$—S-Me | H | H | H | H | 6.6 | 6.0 |
|  | Br | H | H | H | H | 6.9 | 5.8 |
|  | —O—$CH_2$—$CH_2$— |  | H | H | H | 6.4 | 5.5 |
|  | SMe | H | H | H | H | 7.1 | 6.0 |
| 1 | H | F | F | H | H | 6.8 | 5.7 |
| 2 | H | H | H | —OEt | H | 6.8 | <5 |
| 3 | OMe | H | H | H | H | 6.8 | <5 |
| 4 | OEt | H | H | H | H | 7.3 | <5 |
| 5 | H | H | F | H | H | 6.8 | 5.7 |
| 6 | H | F | H | H | H | 6.8 | 5.6 |
| 7 | —$CH_2$—O—Et | H | H | H | H | 7.0 | 5.7 |
| 8 | n-Prop | F | H | H | H | 7.7 | 6.8 |
| 9 | H | H | H | F | H | 7.4 | 5.7 |
| 10 | H | F | H | F | H | 8.1 | 6.2 |
| 11 | n-Prop | H | H | F | H | 8.1 | 6.3 |
| 12 | Br | H | H | F | H | <5 | <5 |
| 13 | H | F | F | H | CH | <5 | <5 |
| 14 | —OEt | H | H | H | CH | 5.26 | <5 |
|  | H | H | H | H | CH | <5 | <5 |

TABLE-continued

| Example No. | R¹ | R² | R³ | R⁴ | R⁵ | 5-HT$_{2C}$ Method a | 5-HT$_{2A}$ Method b |
|---|---|---|---|---|---|---|---|
| 15 | H | H | F | H | CH | 5.37 | <5 |
| 16 | H | F | H | H | CH | 5.36 | <5 |
| 17 | CH$_2$—OEt | H | H | H | CH | <5 | <5 |
| 18 | H | H | H | F | CH | 7.1 | 5.6 |

Penile erection (rats)

It has been shown that penile erection is dependent on the stimulation of 5HT$_{2C}$ receptors (see Berendsen & Broekkamp, Eur. J. Pharm., 135, 179–184 (1987).

The number of penile erections was determined within 45 minutes following the administration of the test substance to the animals. The ED$_{50}$ is the dosage which causes 50% of these erections.

| Example No. | R¹ | R² | R³ | R⁴ | R⁵ | ID$_{50}$ (mg/kg) (p.o.) |
|---|---|---|---|---|---|---|
|  | H | H | H | H | H | 5.0 |
|  | H | H | H | H | CH | 2.0 |
| 1 | H | F | F | H | H | 6.0 |
| 6 | H | F | H | H | H | 3.0 |
| 9 | H | H | H | F | H | 2.9 |
| 16 | H | F | H | H | CH | 1.6 |
|  | —CH$_2$O-i-prop | H | H | H | H | 5.1 |

The compounds of formula I and pharmaceutically acceptable salts thereof can be used as medicaments, e.g. in the form of pharmaceutical preparations. The pharmaceutical preparations can be administered orally, for example, in the form of tablets, coated tablets, dragées, hard and soft gelatine capsules, solutions, emulsions or suspensions. The administration can, however, also be effected rectally, for example, in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Adjuvants such as alcohols, polyols, glycerol, vegetable oils and the like can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a novel compound of formula I or a pharmaceutically acceptable salt thereof and a therapeutically inert excipient are also an object of the present invention, as is a process for the production of such medicaments which comprises bringing one or more novel compounds of formula I or pharmaceutically acceptable salts thereof and, if desired, one or more other therapeutically valuable substances into a galenical administration form together with one or more therapeutically inert carriers. The dosage can vary within wide limits and will, of course, be fitted to the individual requirements in each particular case. In general, in the case of intravenous administration a daily dosage of about 1–1000 mg should be appropriate.

The following Examples are intended to illustrate the manufacture of the specific novel compounds in more detail.

EXAMPLE 1

5,6-Difluorobenzofuran-2-carboxamidine a) 7.29 ml (66.3 mmol) of titanium tetrachloride were added while stirring to a solution, cooled to 0°, of 5.73 g (39.8 mmol) of 3,4-difluoroanisole in 30 ml of anhydrous dichloromethane. Subsequently, the mixture was treated dropwise over 10 minutes with 3.51 ml (39.6 mmol) of 1,1-dichloromethyl methyl ketone and stirred at room temperature for one hour. The mixture was poured into 100 ml of ice-water, extracted twice with 150 ml of dichloromethane each time and the combined organic phases were washed once with 100 ml of water and once with 100 ml of saturated sodium chloride solution. After drying over magnesium sulfate concentration was carried out in a vacuum. The crude product obtained was purified by column chromatography on silica gel (hexane/ethyl acetate 4:1). There were obtained 5.8 g (84%) of 4,5-difluoro-2-methoxybenzaldehyde as a white solid with m.p. 74°.

b) A solution of 5.8 g (33.7 mmol) of 4,5-difluoro-2-methoxybenzaldehyde in 400 ml of anhydrous dichloromethane was treated dropwise at −70° while stirring over a period of 10 minutes with 37 ml (37 mmol) of a 1 M boron tribromide solution in dichloromethane. Subsequently, the mixture was stirred at room temperature for 16 hours, poured on to 400 ml of ice-water and the phases were separated. The aqueous phase was extracted once with 400 ml of dichloromethane and the combined organic phases were washed once with 200 ml of saturated sodium chloride solution, dried over magnesium sulphate and concentrated in a vacuum. The crude product obtained was purified by column chromatography on silica gel (hexane/ethyl acetate 4:1). There were obtained 5.05 g (94%) of 4,5-difluoro-2-hydroxybenzaldehyde as a white solid with m.p. 64°.

c) A mixture of 6.5 g (41.1 mmol) of 4,5-difluoro-2-hydroxybenzaldehyde, 10.4 ml (61.7 mmol) of diethyl bromo-malonate, 11.3 g (82.2 mmol) of potassium carbonate and 50 ml of ethyl methyl ketone was boiled at reflux for 3 hours while stirring, filtered and concentrated in a vacuum. The brown oil obtained was dissolved in 65 ml of ethanol, treated with 6.5 g of potassium hydroxide pellets and heated at reflux for one hour while stirring. The mixture was concentrated in a vacuum and the residue was treated with 65 ml of water and 65 ml of 3N sulfuric acid and heated at reflux over 30 minutes. Subsequently, the mixture was filtered and the residue was washed with water and triturated in 50 ml of hexane over 30 minutes. The solid was filtered off and dried. There were obtained 4.95 g (60%) of 5,6-difluorobenzofuran-2-carboxylic acid as a light yellow solid with m.p. 270°.

d) A mixture of 4.6 g (23.2 mmol) of 5,6-difluorobenzofuran-2-carboxylic acid and 25 ml of thionyl chloride was heated under reflux for 2.5 hours while stirring. Subsequently, the mixture was concentrated in a vacuum, the residue was dissolved in 20 ml of tetrahydrofuran and the solution was added while stirring at room temperature over a period of 10 minutes to a mixture of 20 ml of ammonium hydroxide solution and 100 ml of tetrahydrofuran. The mixture was stirred at room temperature for a further 30 minutes, poured into 150 ml of saturated sodium chloride solution and extracted twice with 250 ml of ethyl acetate each time. The combined organic phases were washed once with 100 ml of saturated sodium chloride solution, dried over magnesium sulfate and concentrated in a vacuum. There were obtained 4.38 g (95%) of 5,6-difluorobenzofuran-2-carboxamide as a beige solid with m.p. 217°.

e) A mixture of 1.4 g (7.1 mmol) of 5,6-difluorobenzofuran-2-carboxamide and 1.62 g (8.5 mmol) of triethyloxonium tetrafluoroborate in 40 ml of anhydrous dichloromethane was stirred at room temperature over 64 hours. Subsequently, the mixture was poured into 70 ml of saturated sodium hydrogen carbonate solution, extracted twice with 100 ml of dichloro-methane each time and the combined organic phases were washed once with 70 ml of saturated sodium hydrogen carbonate solution, dried over magnesium sulfate and concentrated in a vacuum. The brown solid obtained was dissolved in 30 ml of anhydrous ethanol, treated with 2 g of ammonium chloride and heated under reflux for 22 hours. The mixture was diluted with 90 ml of ethyl acetate and extracted three times with 50 ml of water each time. Subsequently, the combined aqueous phases were made basic with 3N sodium hydroxide solution and the solid was filtered off and washed with water. After drying there was obtained 0.55 g (40%) of 5,6-difluorobenzofuran-2-carboxamidine as a white solid with m.p. 178°.

f) 0.55 g (2.8 mmol) of 5,6-difluorobenzofuran-2-carboxamidine was dissolved in 10 ml of methanol-HCl (2.6N) and treated at room temperature while stirring with 100 ml of diethyl ether. The mixture was stirred for a further 3 hours and the white crystals were subsequently filtered off. There was obtained 0.61 g (87%) of 5,6-difluorobenzofuran-2-carboxamidine hydrochloride with m.p. >270°.

EXAMPLE 2

4-Ethoxybenzofuran-2-carboxamidine a) A mixture of 1 g (5.64 mmol) of 4-hydroxybenzofuran-2-carboxamide, 0.5 ml (6.77 mmol) of ethyl bromide, 1.56 g (11.3 mmol) of potassium carbonate, 6 ml of anhydrous DMF and 50 ml of anhydrous acetone was heated at reflux over 24 hours. Subsequently, the mixture was poured on to 70 ml of ice-water, extracted twice with 100 ml of ethyl acetate each time and the combined organic phases were washed once with 100 ml of saturated sodium chloride solution, dried over magnesium sulfate and concentrated in a vacuum. There were obtained 1.15 g (99%) of 4-ethoxybenzofuran-2-carboxamide as a yellow solid with m.p. 113°.

Further reactions were effected analogously to Example 1e–f. 4-Ethoxybenzofuran-2-carboxamidine hydrochloride was obtained as a white solid with m.p. >220°.

EXAMPLE 3

7-Methoxybenzofuran-2-carboxamidine

Analogously to Example 1e–f, starting from 7-methoxybenzofuran-2-carboxamide there was obtained 7-methoxy-benzofuran-2-carboxamidine hydrochloride as a white solid with m.p. >220°.

EXAMPLE 4

7-Ethoxybenzofuran-2-carboxamidine

Analogously to Example 1d–f, starting from 7-ethoxybenzo-furan-2-carboxylic acid there was obtained 7-ethoxybenzofuran-2-carboxamidine hydrochloride as a white solid with m.p. 190°.

EXAMPLE 5

5-Fluorobenzofuran-2-carboxamidine

Analogously to Example 1d–f, starting from 5-fluorobenzo-furan-2-carboxylic acid there was obtained 5-fluorobenzofuran-2-carboxamidine hydrochloride as a white solid with m.p. >250°.

EXAMPLE 6

6-Fluorobenzofuran-2-carboxamidine

Analogously to Example 1d–f, starting from 6-fluorobenzo-furan-2-carboxylic acid there was obtained 6-fluorobenzofuran-2-carboxamidine hydrochloride as a white solid with m.p. >220°.

EXAMPLE 7

7-Ethoxymethylbenzofuran-2-carboxamidine

Analogously to Example 1 e–f, starting from 7-ethoxymethyl-benzofuran-2-carboxamide there was obtained 7-ethoxy-methylbenzofuran-2-carboxamidine hydrochloride as a white solid with m.p. >220°.

The 7-ethoxymethyl-benzofuran-2-carboxamide used was prepared as follows:

a) 4.67 g (16.5 mmol) of ethyl 7-bromomethyl-benzofuran-2-carboxylate were added to a solution of sodium ethanolate in anhydrous ethanol (freshly prepared from 400 mg (17.4 mmol) of sodium in 40 ml of anhydrous ethanol) and the mixture was heated at reflux for one hour. After cooling to room temperature the mixture was poured into 100 ml of 1N HCl and extracted twice with 150 ml of dichloromethane. After drying over magnesium sulfate concentration was carried out in a vacuum. The crude product obtained was purified by column chromatography on silica gel (dichloromethane). There were obtained 2.8 g (69%) of ethyl 7-ethoxymethyl-benzofuran-2-carboxylate as a pale yellow oil.

b) 40 ml of a 25% aqueous ammonium hydroxide solution were added to a solution of 2.8 g (11.3 mmol) of ethyl 7-ethoxymethyl-benzofuran-2-carboxylate in 20 ml of ethanol and the mixture was stirred at room temperature for three hours. The crystals formed were filtered off and dried in a high vacuum. There were thus obtained 1.66 g (67%) of 7-ethoxymethyl-benzofuran-2-carboxamide as a white solid with m.p. 133–134°.

EXAMPLE 8

6-Fluoro-7-propylbenzofuran-2-carboxamidine

Analogously to Example 1c–f, starting from 4-fluoro-2-hydroxy-3-propyl-benzaldehyde there was obtained 6-fluoro-7-propylbenzofuran-2-carboxamidine hydrochloride as a white solid with m.p. >220°.

The 4-fluoro-2-hydroxy-3-propyl-benzaldehyde was prepared as follows:

a) 66.7 ml (106.8 mmol) of a 1.6N butyllithium solution in hexane were added at −78° to a solution of 12 g (95.14 mmol) of 3-fluoroanisole in 240 ml of anhydrous tetrahydrofuran and the mixture was stirred for one hour. Subsequently, 21 ml (288 mmol) of propionaldehyde were added dropwise thereto at −78°, the mixture was stirred for one hour and the solution was left to come to room temperature. The mixture was poured into 240 ml of 1 N HCl and extracted twice with 250 ml of diethyl ether each time. After drying over sodium sulfate concentration was carried out in a vacuum. The crude product obtained was purified by column chromatography on silica gel (dichloromethane/hexane 1:1). There were obtained 15 g (86%) of 1-(2-fluoro-6-methoxy-phenyl)-propan-1-ol as a pale yellow oil.

b) 500 mg of palladium-on-charcoal (10%) were added to a solution of 15 g (81.4 mmol) of 1-(2-fluoro-6-methoxy-phenyl)-propan-1-ol in 200 ml of ethanol and the mixture was hydrogenated at room temperature for 10 hours. The catalyst was filtered off over Dicalite and the filtrate was concentrated in a vacuum. The crude product obtained was purified by column chromatography on silica gel (dichloromethane/hexane 1:2). There were obtained 10.9 g (73%) of 1-fluoro-3-methoxy-2-propyl-benzene as a pale yellow oil.

c) 24 ml (24 mmol) of a 1M boron tribromide solution in dichloromethane were added at −78° to a solution of 3.36 mmol (20 mmol) of 1-fluoro-3-methoxy-2-propyl-benzene in 25 ml of dichloromethane and the mixture was stirred for 10 minutes. After warming to room temperature the mixture was poured cautiously on to 100 ml of ice-water and extracted twice with 250 ml of dichloromethane each time. After drying over sodium sulfate concentration was carried out in a vacuum. The crude product obtained was purified by column chromatography on silica gel (dichloromethane/hexane 4:1). There were obtained 2.9 g (94%) of 3-fluoro-2-propyl-phenol as a pale yellow oil.

d) A solution of 1.4 g (11.7 mmol) of propargyl bromide in 1 ml of dimethylformamide was added dropwise to a suspension of 1.3 g (8.4 mmol) of 3-fluoro-2-propyl-phenol and 1.7 g of potassium carbonate in 4 ml of dimethylformamide and the mixture was subsequently stirred at room temperature for one hour. The mixture was poured on to 30 ml of ice-water and extracted three times with 50 ml of dichloromethane each time. After drying concentration was carried out in a vacuum. The crude product obtained was purified by column chromatography on silica gel (dichloromethane/hexane 1:1). There were obtained 1.45 g (90%) of 1-fluoro-2-propyl-3-prop-2-ynyloxy-benzene as a pale yellow oil.

e) A suspension of 1.5 g (7.8 mmol) of 1-fluoro-2-propyl-3-prop-2-ynyloxy-benzene and 1.7 g (11.15 mmol) of caesium fluoride in 14 ml of diethylaniline was heated at reflux in a metal bath for 4 hours. After cooling to room temperature 100 ml of diethyl ether were added thereto and insoluble constituents were filtered off. The diethyl ether phase was washed three times with 60 ml of 1 N hydrochloric acid, dried over sodium sulfate and concentrated in a vacuum. The crude product obtained was purified by column chromatography on silica gel (dichloromethane/hexane 1:2). There was obtained 0.6 g (40%) of 6-fluoro-2-methyl-7-propyl-benzofuran as a pale yellow oil.

f) Ozone was conducted at −78° into a solution of 4.8 g (25 mmol) of 6-fluoro-2-methyl-7-propyl-benzofuran until the colour became blue. Subsequently, argon was conducted through the solution which was then treated at −78° with 10 ml (136 mmol) of dimethyl sulfide. After warming to room temperature the solution was concentrated in a vacuum and the residue was dissolved in 40 ml of ethanol. After the addition of 20 ml of 3% sodium hydrogen carbonate solution the mixture was stirred at 70° for 30 minutes. Subsequently, the mixture was poured on to 200 ml of ice-water, made acid with 10% HCl and extracted three times with 150 ml of diethyl ether each time. After drying over sodium sulfate concentration was carried out in a vacuum. The crude product obtained was purified by column chromatography on silica gel (dichloromethane). There were obtained 3.3 g (72%) of 4-fluoro-2-hydroxy-3-propyl-benzaldehyde as a pale yellow oil.

EXAMPLE 9

4-Fluoro-benzofuran-2-carboxamidine

Analogously to Example 1c–f, starting from 6-fluoro-2-hydroxybenzaldehyde there was obtained 4-fluoro-benzofuran-2-carboxamidine hydrochloride as a white solid with m.p. >220°.

EXAMPLE 10

4.6-Difluoro-benzofuran-2-carboxamidine

Analogously to Example 1c–f, starting from 2,4-difluoro-6-hydroxy-benzaldehyde there was obtained 4,6-difluoro-benzofuran-2-carboxamidine hydrochloride as a white solid with m.p. >250°.

EXAMPLE 11

4-Fluoro-6-propyl-benzofuran-3-carboxamidine

Analogously to Example 1c–f, starting from 6-fluoro-2-hydroxy-3-propyl-benzaldehyde there was obtained 4-fluoro-6-propyl-benzofuran-3-carboxamidine hydrochloride as a white solid with m.p. 208–210°.

The 6-fluoro-2-hydroxy-3-propyl-benzaldehyde used was prepared as follows:

a) A solution of 42.95 g (0.36 mol) of propargyl bromide in 30 ml of dimethylformamide was added dropwise to a suspension of 50 g (0.26 mol) of 2-bromo-5-fluoro-phenol and 55 g of potassium carbonate in 300 ml of dimethylformamide and the mixture was subsequently stirred at room temperature for two hours. The mixture was poured on to 1500 ml of ice-water and extracted three times with 600 ml of dichloromethane each time. After drying over sodium sulfate concentration was carried out in a vacuum. The crude product obtained was purified by column chromatography on silica gel (dichloromethane/hexane 1:1). 58 g (97%) of 1-bromo-4-fluoro-2-prop-2-ynyloxy-benzene were obtained as a pale yellow oil.

b) A suspension of 57 g (250 mmol) of 1-bromo-4-fluoro-2-prop-2-ynyloxy-benzene and 53 g (350 mmol) of caesium fluoride in 400 ml of diethylaniline was heated at reflux in a metal bath for 4 hours. After cooling to room temperature 1500 ml of diethyl ether were added thereto and the insoluble constituents were filtered off. The diethyl ether phase was washed three times with 600 ml of 1N hydrochloric acid, dried over sodium sulfate and concentrated in a vacuum. The crude product obtained was purified by column chromatography on silica gel (hexane). 51.4 g (89%) of 7-bromo-4-fluoro-2-methylbenzofuran were obtained as a pale yellow oil.

c) A solution of 5.75 g (25.1 mmol) of 7-bromo-4-fluoro-2-methylbenzofuran in 90 ml of tetrahydrofuran was added dropwise to a suspension of 0.625 g (27.5 mmol) of Mg in 100 ml of boiling tetrahydrofuran and the mixture was stirred at reflux for 2.5 hours. Subsequently, it was cooled to 10° C., 2.75 ml (37.5 mmol) of propionaldehyde were added dropwise thereto and the mixture was stirred for 30 minutes. The mixture was poured into 200 ml of 1N hydrochloric acid and extracted three times with 150 ml of dichloromethane. After drying over sodium sulfate concentration was carried out in a vacuum. The crude product obtained was purified by column chromatography on silica gel (dichloro-methane/hexane 4:1). 3.6 g (55%) of 1-(4-fluoro-2-methyl-benzofuran-7-yl)-propan-1-ol were obtained as a pale yellow oil.

d) A suspension of 4.0 g (19.2 mmol) of 1-(4-fluoro-2-methyl-benzofuran-7-yl)-propan-1 -ol and 0.7 g of Pd/C in 60 ml of ethanol was hydrogenated for 2 hours. The catalyst was filtered off, the ethanol was evaporated in a vacuum and the crude product obtained was purified by column chromatography on silica gel (dichloro-methane/hexane 4:1). There were obtained 2.6 g (72%) of a 4:1 mixture of 4-fluoro-2-methyl-7-propyl-benzofuran and 4-fluoro-2-methyl-7-propyl-2,3-dihydro-benzofuran, which was used as such in the next reaction.

e) Ozone was conducted at −78° C. into a solution of 6.6 g (34 mmol) of a 4:1 mixture of 4-fluoro-2-methyl-7-propyl-benzofuran and 4-fluoro-2-methyl-7-propyl-2,3-dihydro-benzofuran until the color became blue. Subsequently, argon was conducted through the solution which was then treated at −78° C. with 13 ml of dimethyl sulfide. After warming to room temperature the solution was concentrated in a vacuum and the residue was dissolved in 50 ml of ethanol. After the addition of 50 ml of 3% sodium hydrogen carbonate solution the mixture was stirred at 70° C. for 30 minutes. Subsequently, the mixture was poured on to 200 ml of ice-water, made acid with 10% HCl and extracted three times with 150 ml of diethyl ether each time. After drying over sodium sulfate concentration was carried out in a vacuum. The crude product obtained was purified by column chromatography on silica gel (dichloromethane/hexane 2:3). There were obtained 5.0 g (100%) of 6-fluoro-2-hydroxy-3-propyl-benzaldehyde as a pale yellow oil, which was used immediately in the next reaction.

EXAMPLE 12

7-Bromo-4-fluorobenzofuran-2-carboxamidine

Analogously to Example 1c–f, starting from 3-bromo-6-fluoro-2-hydroxybenzaldehyde there was obtained 7-bromo-4-fluoro-benzofuran-2-carboxamidine hydrochloride as a white solid with m.p. >230°.

The 3-bromo-6-fluoro-2-hydroxy-benzaldehyde used was prepared as follows:

Ozone was conducted into a solution of 8.0 g (35 mmol) of 7-bromo-4-fluoro-2-methylbenzofuran at −78° C. until the colour became blue. Subsequently, argon was conducted through the solution which was then treated at −78° C. with 13 ml of dimethyl sulfide. After warming to room temperature the solution was concentrated in a vacuum and the residue was dissolved in 50 ml of ethanol. After the addition of 50 ml of 3% sodium hydrogen carbonate solution the mixture was stirred at 70° for 30 minutes. Subsequently, the mixture was poured on to 200 ml of ice-water, made acid with 10% HCl and extracted three times with 150 ml of diethyl ether. After drying over sodium sulfate concentration was carried out in a vacuum. The crude product obtained was purified by column chromatography on silica gel (dichloromethane/hexane 4:1). There were obtained 7.5 g (98%) of 3-bromo-6-fluoro-2-hydroxy-benzaldehyde as a pale yellow oil, which was used immediately in the next reaction.

EXAMPLE 13

5,6-Difluorobenzofuran-2-carboxamidoxime a) 1.5 g (7.61 mmol) of 5,6-difluorobenzofuran-2-carboxamide were treated with 8 ml of phosphorus oxychloride and heated under reflux over a period of 5 minutes while stirring. Subsequently, the clear solution was added dropwise while stirring to a mixture of 36 ml of ammonium hydroxide solution and 64 g of ice, with the temperature not exceeding 20°. The mixture was stirred for a further 30 minutes and the beige crystals were subsequently filtered off. There were obtained 1.2 g (88%) of 5,6-difluorobenzofuran-2-carbonitrile as a beige solid with m.p. 103°.

b) A mixture of 1.2 g (6.7 mmol) of 5,6-difluorobenzofuran-2-carbonitrile, 0.93 g (13.4 mmol) of hydroxylamine hydrochloride, 2.78 g (20.1 mmol) of potassium carbonate and 50 ml of anhydrous ethanol was heated under reflux over 16 hours while stirring. Subsequently, the solid was filtered off and the filtrate was concentrated in a vacuum. The crude product obtained was purified by column chromatography on silica gel (ethyl acetate/hexane 3:2). There was obtained 0.88 g (61%) of 5,6-difluorobenzofuran-2-carboxamidoxime as a light yellow solid with m.p. 184°.

c) 0.88 g (4.15 mmol) of 5,6-difluorobenzofuran-2-carbox-amidoxime was dissolved in 5 ml of methanol-HCl (2.6N) and treated at room temperature while stirring with 100 ml of diethyl ether. The mixture was stirred for a further 4 hours and the white crystals were subsequently filtered off. There were obtained 1.01 g (98%) of 5,6-difluorobenzofuran-2-carboxamidoxime hydrochloride with m.p. 193°.

EXAMPLE 14

7-Ethoxybenzofuran-2-carboxamidoxime

Analogously to Example 13a–c, starting from 7-ethoxy-benzofuran-2-carboxamide there was obtained 7-ethoxybenzofuran-2-carboxamidoxime hydrochloride as a light yellow solid with m.p. 171°.

EXAMPLE 15

5-Fluorobenzofuran-2-carboxamidoxime

Analogously to Example 13a–c, starting from 5-fluoro-benzofuran-2-carboxamide there was obtained 5-fluorobenzofuran-2-carboxamidoxime hydrochloride as a white solid with m.p. 203–204°.

EXAMPLE 16

6-Fluorobenzofuran-2-carboxamidoxime

Analogously to Example 13a–c, starting from 6-fluoro-benzofuran-2-carboxamide there was obtained 6-fluorobenzofuran-2-carboxamidoxime hydrochloride as a white solid with m.p. 224–225°.

EXAMPLE 17

7-Ethoxymethylbenzofuran-2-carboxamidoxime

Analogously to Example 13a–c, starting from 7-ethoxy-methylbenzofuran-2-carboxamide there was obtained 7-ethoxy-methylbenzofuran-2-carboxamidoxime hydrochloride as a white solid with m.p. 200–202°.

EXAMPLE 18

4-Fluorobenzofuran-2-carboxamidoxime

Analogously to 13a–c, starting from 4-fluorobenzofuran-2-carboxamide there was obtained 4-fluorobenzofuran-2-carboxamidoxime hydrochloride as a white solid with m.p. 186–188°.

EXAMPLE A

Tablets of the following composition are produced in the usual manner:

|  | mg/Tablet |
|---|---|
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in the usual manner:

|  | mg/Tablet |
|---|---|
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
|---|---|
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

We claim:

1. A method of controlling or treating migraine, schizophrenia, anxiety states, sleep disorders, anorexia, Alzheimer's disease, addictions or disorders which result from damage to the head or brain or to the spinal column or bone marrow in a host requiring such control or treatment, comprising administering to the host an effective amount of a compound of the formula

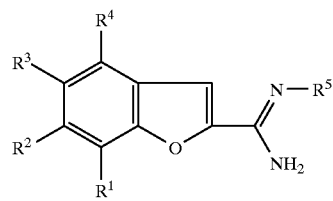

wherein $R^1$–$R^4$ are, independently, hydrogen, halogen, lower-alkyl, lower-alkoxy, aryl, benzyloxy, lower-alkoxy-lower-alkyl, lower-alkyl-sulphanyl, lower-alkyl-sulphanyl-lower-alkyl or $R^1$ and $R^2$ together are the group —O—$(CH_2)_2$— or $(CH_2)_2$—O; and $R^5$ is hydrogen or hydroxy, or a pharmaceutically acceptable salt thereof.

2. The method of claim 1, wherein $R^1$, $R^2$, $R^3$ and $R^4$ are hydrogen.

3. The method of claim 1, wherein $R^5$ is hydrogen.

4. The method of claim 3, wherein $R^1$ and $R^4$ are hydrogen and $R^2$ and $R^3$ are fluorine.

5. The method of claim 3, wherein $R^1$, $R^2$ and $R^3$ are hydrogen and $R^4$ is ethoxy.

6. The method of claim 3, wherein $R^1$ is methoxy and $R^2$ and $R^3$ are hydrogen.

7. The method of claim 3, wherein $R^1$ is ethoxy and $R^2$, $R^3$ and $R^4$ are hydrogen.

8. The method of claim 3, wherein $R^1$, $R^2$ and $R^4$ are hydrogen and $R^3$ is fluorine.

9. The method of claim 3, wherein $R^1$, $R^3$ and $R^4$ are hydrogen and $R^2$ is fluorine.

10. The method of claim 3, wherein $R^1$ is methyloxyethyl and $R^2$, $R^3$ and $R^4$ are hydrogen.

11. The method of claim 3, wherein $R^1$ is n-propyl, $R^2$ is fluorine, and $R^3$ and $R^4$ are hydrogen.

12. The method of claim 3, wherein $R^1$, $R^2$ and $R^3$ are hydrogen and $R^4$ is fluorine.

13. The method of claim 1, wherein $R^5$ is hydroxy.

14. The method of claim 2, wherein $R^1$ and $R^4$ are hydrogen and $R^2$ and $R^3$ are fluorine.

15. The method of claim 12, wherein $R^1$ is ethoxy and $R^2$, $R^3$ and $R^4$ are hydrogen.

16. The method of claim 13, wherein $R^1$, $R^2$ and $R^4$ are hydrogen and $R^4$ is fluorine.

17. The method of claim 13, wherein $R^1$, $R^3$ and $R^4$ are hydrogen and $R^2$ is fluorine.

18. The method of claim 13, wherein $R^1$ is methyloxyethyl and $R^2$, $R^3$ and $R^4$ are hydrogen.

* * * * *

UNITED STATES PATENT AND TRADEMARK OFFICE
CERTIFICATE OF CORRECTION

PATENT NO. : 5,955,495
DATED : September 21, 1999
INVENTOR(S) : Bos, et al.

It is certified that error appears in the above-indentified patent and that said Letters Patent is hereby corrected as shown below:

COVER PAGE:

Foreign Application Priority data is not listed. The Foreign Application Priority data should read --- [30] Foreign Application Priority Data
    96106990    5/03/96    European Pat. Off. --

Signed and Sealed this

Twenty-third Day of May, 2000

Attest:

Q. TODD DICKINSON

*Attesting Officer*      *Director of Patents and Trademarks*